(12) United States Patent
Sampson

(10) Patent No.: US 7,156,109 B2
(45) Date of Patent: Jan. 2, 2007

(54) SMOKING CESSATION ORAL HYGIENE DEVICE

(76) Inventor: Mark A. Sampson, 870 Rockwood Dr., Titusville, PA (US) 16354

( * ) Notice: Subject to any disclaimer, the term of this patent is extended or adjusted under 35 U.S.C. 154(b) by 142 days.

(21) Appl. No.: 10/215,349

(22) Filed: Aug. 8, 2002

(65) Prior Publication Data

US 2004/0025900 A1    Feb. 12, 2004

(51) Int. Cl.
*A61C 15/00* (2006.01)
(52) U.S. Cl. ............. 132/323; 132/329; 132/321
(58) Field of Classification Search ......... 132/321–329
See application file for complete search history.

(56) References Cited

U.S. PATENT DOCUMENTS 4,194,290 A * 3/1980 Vallhonrat ............... 433/141
5,035,252 A * 7/1991 Mondre .................. 132/321
5,392,795 A * 2/1995 Gathani .................. 132/323
5,842,489 A * 12/1998 Suhonen et al. ......... 132/321

FOREIGN PATENT DOCUMENTS

JP          407100453 A  *  4/1995  ............ 132/321

* cited by examiner

*Primary Examiner*—John J. Wilson
*Assistant Examiner*—Robyn Doan
(74) *Attorney, Agent, or Firm*—Charles N. Quinn, Esq.

(57) ABSTRACT

The present invention relates to an improved combination tooth pick/dental floss appliance, with the addition of, a food and or medicament pad. The tasks carried out by the invention are beyond basic flossing to include the delivery system of an attached medicament such as or combination of, nicotine, breath fresheners, antacids, fluoride, and teeth brighteners. This invention is most valuable to a person on the go, who does not have easy access to facilities to brush their teeth as desired. This combination dental tool with the accompanying medicament gives one the ability to cleanse one's teeth as well as freshen one's mouth whether it be after eating or smoking.

31 Claims, 1 Drawing Sheet

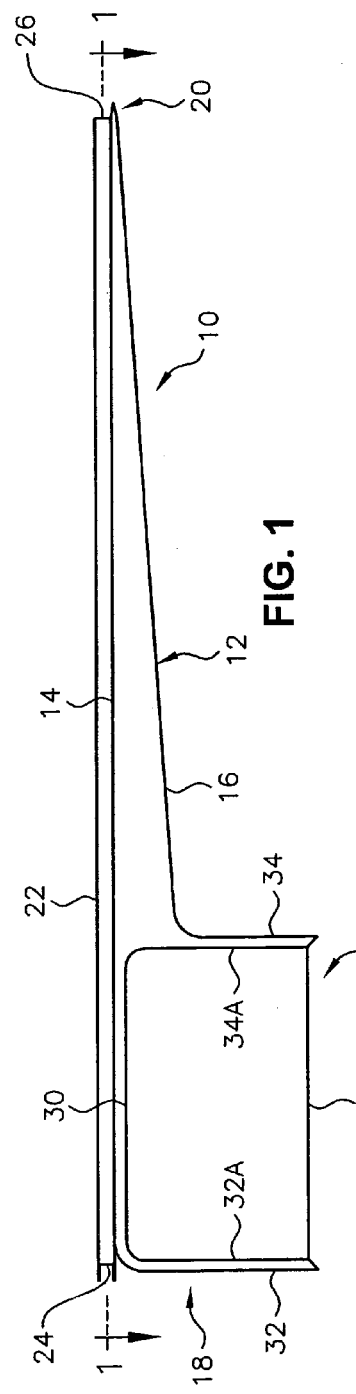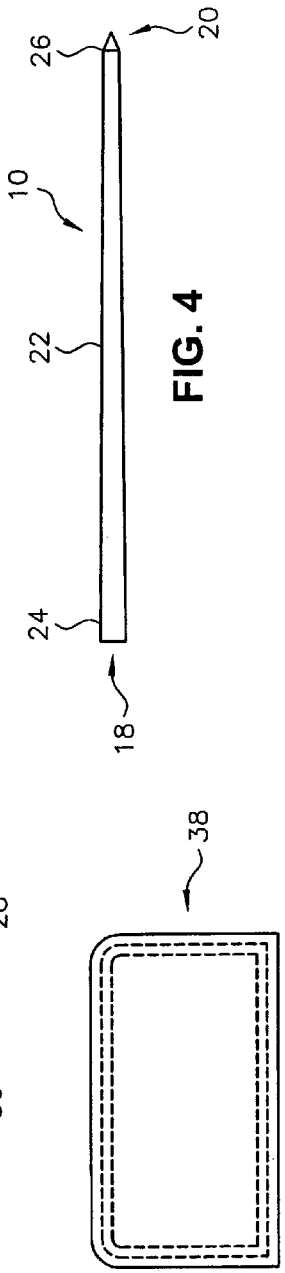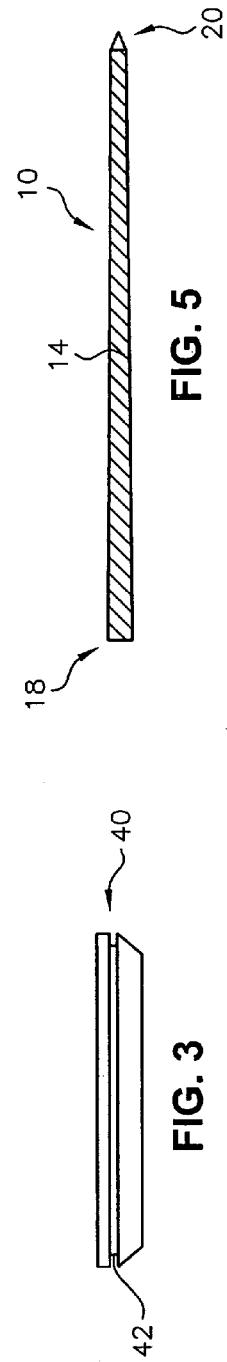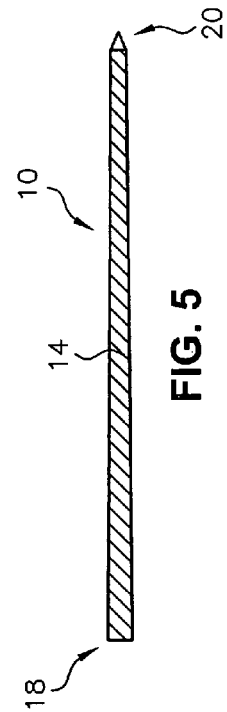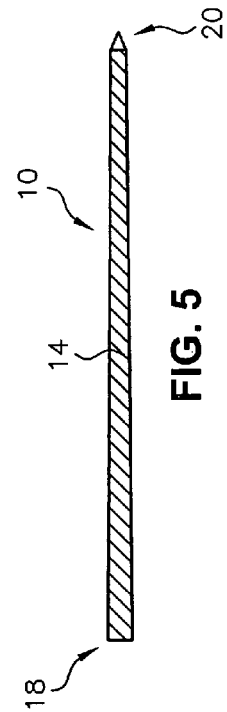

SMOKING CESSATION ORAL HYGIENE DEVICE

FIELD OF THE INVENTION

The present invention relates to an improved combination tooth pick/dental floss appliance, with the addition of a medicament pad.

DESCRIPTION OF PRIOR ART

An ever important part of our acceptance and success in society today is placed upon our ability to interact and communicate with others. Our success in this highly interactive world mandates a person has many controls. Clean proper dress, good hair grooming, as well as control over the perception of ones own breath. An important part of our social acceptance is placed on the appearance of our teeth, freshness of breath, and on our overall oral hygiene. It is not uncommon to be placed into a confined situation with others and be totally unprepared concerning ones oral state.

A large percentage of the population, being the baby boomers, were taught both in school and at home about the importance of brushing ones teeth. This generation, for the most part was later introduced to benefits of using dental floss. Many still have a fear and misunderstanding of flosses and flossing tools. The benefits of dental floss, such as controlling gum disease, fighting bad breath, and aiding in plaque removal are unquestioned. It would only make sense that more and more of the population is finding a method for using floss that is suited to them.

Over the course of time many different techniques have been put to use in the development of floss containers and applicators. Related art shows the development of many inventions starting with simple spool like products to complex floss applicators with built in storage compartments. An example of a complex flossing apparatus is represented in U.S. Pat. No 5,423,338 ('338) to Hodge comprising a device shaped similar to an electric toothbrush, which holds the dental floss in a sealed enclosure to prevent contamination of the unused floss. This particular product represents a less portable and more cumbersome device more suitable for a stationary environment. It is reasonable to assume that situations will arise where it is impractical, whether by time constraints or physical location, for a person to brush or to floss one's teeth using such a large appliance represented in the '338 patent. The '338 patent and others like it, lend themselves to a terrible disadvantage for those persons unable to stop their day's activities to find facilities in which to use these products.

A major category of previous flossing devices and theoretically a more desirable appliance, geared to persons on the move, would be reflected in the related art of disposable floss tools; an example of one such patent is U.S. Pat. Des. No. 279,826 to Schindler. Some of the obvious advantages of this style of tools include their ease of use, portability, compact size, as well as affordability.

One constraint of all prior art concerning floss holding devices is their inability to act as delivery system of a medicament. A device that incorporates the convenience of a floss tool combined with a medicament, gives the added benefits of that particular medicament.

SUMMARY OF THE INVENTION

The present invention is a smoking cessation and oral hygiene device facilitating tooth cleaning by the use of dental floss. The device can used as a smoking cessation device or an oral hygiene device depending on the necessity of the user.

The preferred embodiment comprises one-piece integral construction having an elongated handle tapering from a floss and medicament holding end to a remote pointed toothpick end. The floss and medicament end form the base of a U-shaped portion having extremities in the form of parallel legs. The legs are deformable to allow for the insertion of the medicament pad therebetween and are spaced apart the width of a large adult's 12 year molar. The U-shaped portion is sufficiently small to fit easily into the mouth of an adolescent.

A saliva-soluble orally administered hygienic medicament pad is secured to the U-shaped portion. In the preferred embodiment, the medicament pad can be designed as a nicotine delivery system, which reduces and thereafter eliminates the craving for nicotine and smoking. Thus, a series of medicament pads could be produced each having a reduced amount of nicotine to wean the smoker from the biochemical cravings associated with smoking.

The present invention not only satisfies the biochemical craving associated with nicotine but also simulates the physical actions of smoking by the elongated handle being placed within the finger tips of the user. Moreover, it is logical to combine an oral hygiene tool with a smoking cessation device because smoking is a habitual activity after eating.

The present invention is not limited to use by smokers. A non-smoker may use a mint type flavored medicament which will freshen the users breath; an antacid medicament which will aid in the acid reflux experienced by many; or a fluoride medicament which will help prevent cavity production. The variety of flavors and ingredients of the attached medicament pad entices the task of flossing resulting in improved oral hygiene.

Dental floss is connected to and extends between the legs of the U-shaped portion spaced from the extension portion of the elongated handle forming said base of the U-shaped portion.

It is an object of this invention to define a combination floss applicator and tooth pick apparatus with a medicament attachment, which satisfies the biochemical and physical cravings of smoking.

It is another object of the invention to make known a smoking cessation and oral hygiene device used as an enticement for flossing and proper dental hygiene.

It is another object of the invention to make known a smoking cessation and oral hygiene device which produces freshened breath.

BRIEF DESCRIPTION OF THE DRAWINGS

FIG. 1 is a side view of the smoking cessation device devoid of a medicament pad.

FIG. 2 is a side view of the medicament pad.

FIG. 3 is a top view of the medicament pad illustrating the beveled edge

FIG. 4 is a top view of the device.

FIG. 5 is a top view of the device cut along the lines 1—1 of FIG. 1.

DETAILED DESCRIPTION OF THE INVENTION

Referring now to FIGS. 1–5, the smoking cessation oral hygiene device 10 is of one-piece integral construction having an elongated handle 12, with a top end 14 and a bottom end 16, tapering from a floss and medicament holding end 18 to a remote pointed toothpick end 20. An air drawing tube 22, having a proximal end 24 and a distal end 26, is integral with the top end 14 of the elongated handle 12. A U-shaped portion 28 defining said floss and medicament holding end 18 has a base 30 formed as an extension portion of said handle 12. Extremities as proximal 32 and distal 34 legs of said base 30 are adapted to retain dental floss 36 stretched therebetween. The U-shaped portion 28 is sufficiently small to fit easily into the mouth of an adolescent. The proximal 32 and distal 34 legs of the U-shaped portion 28 are structurally deformable and spaced apart the width of a large adult's 12 year molar.

As best illustrated in FIGS. 2 and 3, the preferred embodiment of the medicament pad 38 is cast as two disc halves 40 which are joined with edible adhesive (not shown) encompassing, and attaching to, the U-shaped portion 28. Additionally, the medicament pad 38 can be manufactured having a beveled edge 42 on the disc halve 40, which is complementary to the interior of the legs 32A, 34A and base 30A of the U-shaped portion 28. This allows for the mating of the surfaces of the interior of the legs 32A, 34A, and base 30A with the beveled edge 42 of the medicament pad 38. The mating surfaces of the interior of the legs 32A, 34A, base 30A and medicament pad 38 can be of a variety of complementary configuration such as V-shaped, U-shaped or a simple groove.

Other possible attachments methods of the medicament pad include dipping the device 10 into a liquid solution of the desired medicament coating to form a medicament pad 38. When the proper coating thickness is achieved the device 10 is left to dry and the resultant being a device 10 with a dissolvable coating.

The physical attachment methods are known in the art and depend on the particular medicament being used. The particular attachment method used with a particular medicament, will be selected to ensure the manufacturing of the device is practical and economically viable.

The device is most often used after eating by placing the U-shaped portion 28 of the elongated handle 12 into the user's mouth and ejecting any remaining food material by using the toothpick end 20 and thereafter, the dental floss 36 in the usual flossing practice. As the user is flossing, the medicament pad 38 is being dissolved by saliva and "usual sucking" motion of the mouth.

In the preferred embodiment, when the device 10 is being used to reduce or eliminate smoking, the substances of the medicament pad 38 are released by the usual "sucking motion" of the mouth as the user draws in air through the air drawing tube 22 integral with the elongated handle 12. Simultaneously, the elongated handle 12 is being grasped by the fingers of the user. The inhalation of the substance in the medicament pad 38 and the grasping of the elongated handle 12 of the device 10, satisfy both the biochemical cravings and physical behavior characteristics associated with smoking, enabling the smoker to eliminate the behavior.

What is claimed is:

1. A smoking cessation apparatus facilitating dental floss-based tooth cleaning and oral hygiene, comprising:
   a. a frame of one-piece integral construction including:
      i. an elongated handle tapering from a floss and medicament holding end to a remote pointed toothpick end; and
      ii. a U-shaped portion defining said floss and medicament holding end having a base of the U formed as an extension portion of said handle, extremities of legs of said U being adapted to retain dental floss stretched therebetween, said U-shaped portion being sufficiently small to fit easily into the mouth of an adolescent, said legs of said U being spaced apart than width of a large adult's 12 year molar;
   b. dental floss connected to and extending between said legs of said U proximate extremities thereof and spaced from said extension portion of said handle forming said base of said U;
   c. a saliva-soluble orally administered hygienic medicament secured at least to said U-shaped portion; and
   d. an air drawing tube integral with said elongated handle wherein said U-shaped portion includes at least one first mating surface and said medicament includes at least one second mating surface, said mating surface complementally contactingly engaging each other to retain said medicament in position on said frame.

2. Apparatus of claim 1 wherein said first mating surface is formed in the legs of said U-shaped portion.

3. Apparatus of claim 2 wherein said first mating surface includes a groove.

4. Apparatus of claim 3 wherein said first mating surface groove is U-shaped.

5. Apparatus of claim 4 wherein said first mating surface comprises a pair of facing, convergingly sloping sides formed in said U-shaped member.

6. Apparatus of claim 5 wherein said first mating surface includes an undercut formed at the position of maximum proximity of said respective sloping sides.

7. Apparatus of claim 6 wherein said first mating surface is a step.

8. Apparatus of claim 7 wherein said first and second mating surfaces are complementally shaped steps.

9. Apparatus of claim 3 wherein said first mating surface groove has a V-shaped interior.

10. Apparatus of claim 2 wherein there are a plurality of first mating surfaces communicating with extremities of said legs of said U-shaped portion remote from said base.

11. Apparatus of claim 10 wherein said first mating surfaces face one another.

12. Apparatus of claim 10 wherein said first mating surfaces extend the lengths of said legs of said U.

13. Apparatus of claim 10 wherein said first mating surfaces face in a common direction.

14. Apparatus of claim 10 wherein said first mating surfaces face in opposite directions.

15. Apparatus of claim 2 wherein said first mating surfaces communicate with extremities of said legs of said U at said base of said U.

16. Apparatus of claim 1 wherein said first mating surface is formed in the base of said U-shaped portion.

17. Apparatus of claim 1 wherein said first mating surface extends parallel to said handle.

18. Apparatus of claim 1 wherein said medicament includes a nicotine substance.

19. Apparatus of claim 1 wherein said medicament includes a fluoride-based tooth enamel hardener.

20. Apparatus of claim 1 wherein said medicament includes a breath freshener.

21. Apparatus of claim 1 wherein said medicament includes a base for neutralizing stomach acid.

22. Apparatus of claim 1 wherein said medicament includes a stomach acid production inhibitor.

23. Apparatus of claim 1 wherein said medicament includes a tooth enamel whitener.

24. Apparatus of claim 23 wherein corresponding sides of said handle and said U-shaped portions are co-planar.

25. Apparatus of claim 1 wherein said medicament has a groove formed in the periphery thereof for matingly contacting said U-shaped portion of said frame.

26. Apparatus of claim 25 wherein said groove is formed on three sides of said medicament.

27. Apparatus of claim 25 wherein said groove is formed on and extends the length of at least one side of said medicament.

28. A smoking cessation apparatus facilitating dental floss-based tooth cleaning and oral hygiene, comprising:
   a. a frame of one-piece integral construction including:
      i. an elongated handle tapering from a floss and medicament holding end to a remote pointed toothpick end; and
      ii. a U-shaped portion defining said floss and medicament holding end having a base of the U formed as an extension portion of said handle, extremities of legs of said U being adapted to retain dental floss stretched therebetween, said U-shaped portion being sufficiently small to fit easily into the mouth of an adolescent, said legs of said U being spaced apart than width of a large adult's 12 year molar;
   b. dental floss connected to and extending between said legs of said U proximate extremities thereof and spaced from said extension portion of said handle forming said base of said U;
   d. a saliva-soluble orally administered hygienic medicament secured at least to said U-shaped portion; and
   e. an air drawing tube integral with said elongated handle;
   wherein said legs of said U-shaped portion are sufficiently elastically deformable that when said medicament is pressed into place between said legs, said legs deform and elastically press against said medicament to retain the medicament in place therebetween.

29. Apparatus of claim 28 wherein said frame has planar sides.

30. Apparatus of claim 28 wherein said frame has at least one planar side.

31. Apparatus facilitating dental floss-based tooth cleaning and oral hygiene, comprising:
   a. a frame of one-piece integral construction including:
      i. an elongated handle tapering from a floss and medicament holding end to a remote pointed toothpick end; and
      ii. a U-shaped portion defining said floss and medicament holding end having a base of the U formed as an extension portion of said handle, extremities of legs of said U being adapted to retain dental floss stretched therebetween, said U-shaped portion being sufficiently small to fit easily into the mouth of an adolescent, said legs of said U being spaced apart than width of a large adult's 12 year molar;
   b. dental floss connected to and extending between said legs of said U proximate extremities thereof and spaced from said extension portion of said handle forming said base of said U;
   c. a saliva-soluble orally administered hygienic medicament secured at least to said U-shaped portion; and
   d. an air drawing tube integral with said elongated handle, wherein said U-shaped portion includes first mating surfaces and said medicament includes at least one second mating surface, said mating surfaces complementally contactingly engaging each other to retain said medicament in position on said frame;
   wherein said legs of said U-shaped portion are sufficiently elastically deformable that when said medicament is pressed into place between said legs, said legs deform and elastically press against said medicament to retain the medicament in place therebetween;
   wherein said first mating surfaces are formed in the legs of said U-shaped portion;
   wherein said first mating surfaces include grooves;
   wherein said first mating surfaces face one another;
   wherein said first mating surfaces extend in a common direction substantially the lengths of said legs of said U;
   wherein said first mating surfaces communicate with extremities of said legs of said U at said base of said U;
   wherein said medicament includes a fluoride-based tooth enamel hardener,
   wherein said medicament includes a breath freshener and a base for neutralizing stomach acid, a stomach acid production inhibitor, and a tooth enamel whitener;
   wherein said frame has planar sides;
   wherein each first mating surface groove is U-shaped and comprises a pair of facing, convergingly sloping sides formed in said U-shaped member and further includes an undercut formed at the position of maximum proximity of said respective sloping sides;
   wherein said medicament has a groove formed in the periphery thereof for matingly contacting and engaging said U-shaped portion of said frame.

* * * * *